United States Patent [19]
Yokota et al.

[11] Patent Number: 5,854,370
[45] Date of Patent: Dec. 29, 1998

[54] EPOXY RESIN STILBENES AND PROCESS FOR PRODUCING THE SAME BY PHOTOISOMERIZATION

[75] Inventors: Akira Yokota; Yasuhiro Hirano; Masatsugu Akiba; Hiroshi Nakamura; Shigeki Naitoh, all of Ibaraki, Japan

[73] Assignee: Sumitomo Chemical Company, Limited, Osaka, Japan

[21] Appl. No.: 863,300

[22] Filed: May 27, 1997

Related U.S. Application Data

[62] Division of Ser. No. 657,363, Jun. 3, 1996, Pat. No. 5,705,596.

[30] Foreign Application Priority Data

Jun. 2, 1995 [JP] Japan ................... 7-136760

[51] Int. Cl.$^6$ .................. C07D 303/24; C08G 59/24
[52] U.S. Cl. ............ 528/101; 522/170; 549/560; 204/157.64; 204/157.65; 204/157.69; 204/157.82; 204/157.92
[58] Field of Search ............ 204/157.64, 157.65, 204/157.69, 157.82, 157.92; 522/170; 528/101; 549/560

[56] References Cited

U.S. PATENT DOCUMENTS

| | | | |
|---|---|---|---|
| 4,462,901 | 7/1984 | Dhein | 528/73 |
| 5,266,405 | 11/1993 | Kirchmeyer | 428/413 |
| 5,460,860 | 10/1995 | Hefner et al. | 428/1 |

FOREIGN PATENT DOCUMENTS 2 041 221  3/1972  Germany .

OTHER PUBLICATIONS

Griffith, James R., 'Epoxy Resins Containing a Specific Vulnerablity', ACS Symposium Series, vol. 114, pp. 259–262 (1979).

Osada & Katsumura, 'Photomechanochemical Energy Conversion in a Polyamide Containing a Stilbene Structure in the Backbone', Makromol. Chem., Rapid Commun. 2, pp. 441–415 (1981).

Chemical Abstracts 112:66404, "influence of Polar Solvents on Reaction Dynamices: Photoisomerization Studies of Dihydroxystilbene", Park et al.

*Primary Examiner*—Frederick Krass
*Attorney, Agent, or Firm*—Pillsbury Madison & Sutro LLP

[57] ABSTRACT

The invention provides a cis-stilbene type epoxy resin having lower melting point and lower viscosity than the trans-stilbene type epoxy resin hitherto known. The stilbene type epoxy resin has a cis-isomer content of essentially 100%, or in the alternative, at least about 10% with the rest being the trans-isomer, and is based on the following general formula (1):

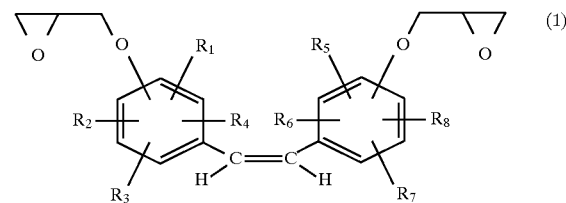

wherein $R_1$ to $R_8$ are independently an acyclic or cyclic alkyl group, a hydrogen atom, or a halogen atom. Production processes for these epoxy resins are also disclosed.

10 Claims, 1 Drawing Sheet

EPOXY RESIN STILBENES AND PROCESS FOR PRODUCING THE SAME BY PHOTOISOMERIZATION

This is a division of application Ser. No. 08/657,363, filed Jun. 3, 1996, now U.S. Pat. No. 5,705,596.

FIELD OF THE INVENTION

The present invention relates to an epoxy resin and a process for producing the same. This epoxy resin is useful for adhesives, paints, and electric and electronic materials such as insulation materials and laminated plates, and is particularly useful for encapsulating electronic devices.

BACKGROUND OF THE INVENTION

A plethora of publications extant about stilbene-containing epoxy resins exist. In general, a stilbene linkage can be substituted or unsubstituted and can exist in the cis or trans form. Epoxy resins having an unsubstituted stilbene skeleton are disclosed in, for example, ACS Symposium Series 114, Chapter 17, pp. 259–262 (176th Meeting of the American Chemical Society (1978)). Glycidyl ether derivatives of bisphenol compounds having a stilbene skeleton are known. These can be unsubstituted or substituted by, for example, alkyl groups, and preferably, symmetrically substituted by methyl groups. Such derivatives are disclosed in the patent literature including U.S. Pat. No. 4,762,901, German patent No. 3622613, and Japanese published Kokai (Laid Open) application No. 63-23931.

However, with respect to hitherto disclosed epoxy resins having a stilbene skeleton, there has been no distinction nor much recognition of any useful difference between the trans-isomer and the cis-isomer of the stilbene linkage.

The stilbene skeleton obtained by conventional processes is 100% or essentially 100% the trans-isomer. A conventional process for preparing stilbene compounds is described in, for instance, Liebigs Ann. Chem., 730, 31–46 (1969).

Trans-stilbene type epoxy resins have problems which limit their use including poor efficiency in processing operations. For example, because of the high melting points of the trans-stilbene type resins in general, working process techniques such as kneading and the like become very difficult. More specifically, the glycidyl derivatives of 4,4'-dihydroxystilbene, 4,4'-dihydroxy-3, 3'-dimethylstilbene, and 4,4'-dihydroxy-3,3', 5,5'-dimethylstilbene have high melting points of 208°–215° C., 150° C., and 151° C. respectively. Consequently, it is difficult to mix these compounds homogeneously with epoxy curing agents and to knead these resins with other components. In the melt state, however, stilbene-type epoxy resins have a comparatively low viscosity making it relatively easy to knead them with other components. A further lowering of the viscosity would mean further improvement in the efficiency of the kneading process.

Therefore, there has been a need for stilbene-type epoxy resins having lower melting points and viscosities suitable for demanding industrial applications such as encapsulating semiconductor components and semiconductor devices. In particular, melting points less than about 150° C. and viscosities less than about 0.2 poise at 150° C. would be desirable.

SUMMARY OF THE INVENTION

In view of the above situation, the present inventors conducted extensive research directed towards means for controlling the properties of the stilbene type epoxy resins including, for example, lowering the melting point and viscosity. As a result, the present inventors solved these and other needs by an improved stilbene-type epoxy resin which has a lower melting point and a lower viscosity than the hitherto conventional resins based on the trans-isomer.

The present inventors have discovered that a stilbene-type epoxy resin composition containing more than a certain amount of the cis-isomeric form of stilbene linkage satisfies the twin objectives of lower melting point and lower melt viscosity. Specifically, good results are achieved when a cis-isomer content greater than about 10% is present. Cis-isomeric forms of the stilbene linkages can be prepared from corresponding trans-isomeric forms by photoisomerization. Photoisomerization can be executed on epoxy-group containing stilbenes or on phenolic stilbenes compounds which are then converted to epoxy resins.

Advantages of the present invention include the ability to lower and tailor the melting temperature and melt viscosity of the epoxy resins.

DETAILED DESCRIPTION OF THE INVENTION

Figure 1:
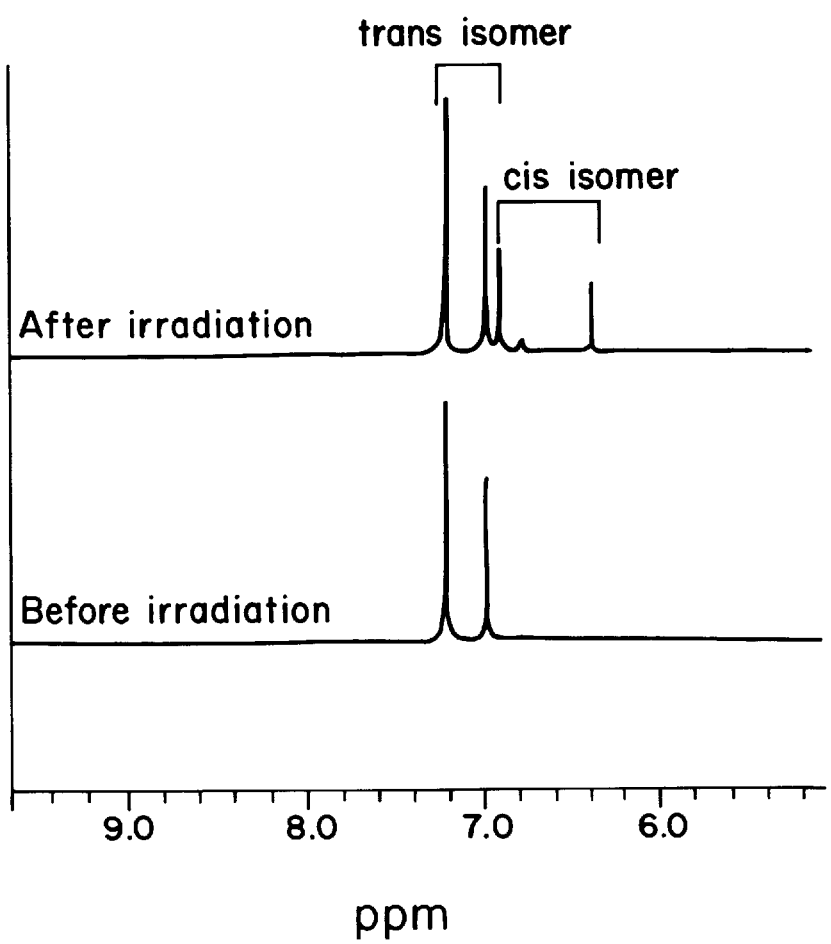
FIG. 1 shows $^1$H-NMR spectrum of a stilbene composition before and after the photoisomerization reaction as disclosed in Example 1.

Epoxy precursor resins can be cured to yield epoxy resins by methods known to those skilled in the art. Precursor resin means that further reaction of the resin is possible, if desired, to yield a cured epoxy resin. In general, an epoxy precursor resin will still have unreacted epoxy groups, although in some cases, some epoxy groups may be already reacted. A cured epoxy resin will generally contain few if any unreacted epoxy groups. For partially cured epoxy resins, only some of the epoxy groups are reacted in the cure. The generic term epoxy resin herein is defined to encompass all of these forms of the resin including precursor, partially cured, and cured forms.

An epoxy precursor resin according to the present invention can be based on or include compounds represented by the general formula (1):

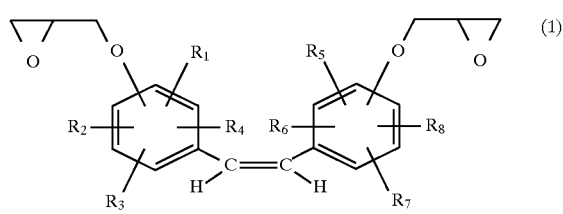

wherein $R_1$ to $R_8$ independently can be, for example, an acyclic or cyclic alkyl group having 1 to 6 carbon atoms, a hydrogen atom, or a halogen atom. Formula (1) shows the cis-isomer, and the epoxy resin or precursor resin can include essentially 100% cis-isomer content, or in the alternative, at least about 10% cis-isomer content with the remainder being the trans-isomer. Although 100% cis-isomer content may be desired in some cases, there inevitably may be small amounts of the trans-isomer depending on the processing conditions and the purification procedures.

The invention also encompasses a process for producing the epoxy precursor resin represented by general formula (1) which comprises the step of irradiating with ultraviolet light a corresponding trans-stilbene type epoxy precursor resin represented by the general formula (2):

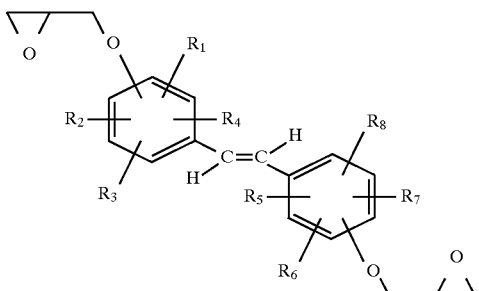

wherein $R_1$ to $R_8$ are defined in the same terms as for general formula (1).

Another process for producing the epoxy precursor resin represented by formula (1) comprises the step of irradiating stilbene phenolic compounds with ultraviolet light, and in particular, trans-stilbene phenolic compounds represented by the general formula (3):

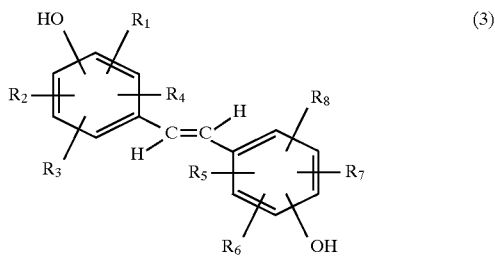

wherein $R_1$ to $R_8$ are defined in the same terms as for formula (1). Irradiation yields at least some formation of a stilbene type phenolic compound represented by the general formula (4) consisting of cis-isomer:

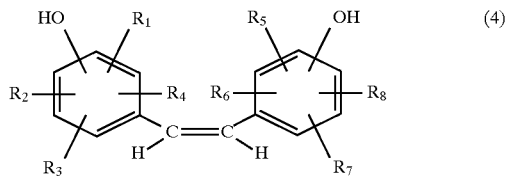

wherein $R_1$ to $R_8$ are defined in the same terms as for formula (1). The cis-isomer content may be essentially 100%, or in the alternative, may be at least 10% with the rest consisting of the trans-isomer. Phenolic stilbene compounds are defined herein as stilbene compounds substituted with hydroxy groups on the aromatic ring which allows for conversion of the hydroxy functional group to an epoxy functional group. Epoxy precursor resins can be prepared from the phenolic stilbene compounds by, for example, reaction with epihalohydrin in the presence of base as known to those of skill in the art. For each of these embodiments, the person skilled in the art can control the amount of cis-isomer content by, for example, controlling the irradiation and purification procedures, as well as by controlling the reaction and processing conditions.

The aforementioned substituents represent preferred embodiments, but in addition, substituents, $R_1$–$R_8$, for the stilbene type epoxy resins represented by formulas (1) and (2) and phenolic compounds represented by formulas (3) and (4) can be varied diversely if so desired. Substituents can be selected independently of each other. There is no particular limitation to the selection provided that desirable features of the invention are not compromised. In general, lower melt viscosities are desirable. For instance, substituents can be of lower molecular weight such as, for example, a $C_1$–$C_{10}$ substituent, or preferably, a $C_1$–$C_6$ substituent. Examples of lower molecular weight substituents include a hydrogen atom, a halogen atom, and alkyl or cycloalkyl groups. Representative alkyl groups include methyl, ethyl, propyl, butyl, amyl, cyclopentyl, hexyl, and cyclohexyl, and also include all isomers of these alkyl groups such as iso-propyl and tert-butyl. Halogen substituents include the chlorine and bromine atoms. The substituents are preferably hydrogen, methyl, ethyl, propyl, and butyl groups because of the low melt viscosity of the products and the availability of raw materials. If desired, the substituents may be derivatized or may be reactive so as to modify the properties of the epoxy resin.

The stilbene type epoxy resins or precursor resins consisting of 100% cis-isomer content, or in the alternative, at least 10% cis-isomer content (formula 1) can be produced by photoisomerization with ultraviolet light of trans-stilbene type epoxy resins consisting of resins represented by formula (2). The trans-stilbene type epoxy resin represented by the general formula (2) can be prepared by well-known processes. For example, glycidyl etherification of a phenol derivative can be carried out by procedures described in, for instance, JP-B-63-33769, the complete disclosure of which is incorporated herein by reference. In other words, the epoxy resin is obtainable from the reaction of the trans-stilbene type phenol with epihalohydrin in the presence of a suitable base, such as an alkali of which sodium hydroxide, potassium hydroxide, calcium hydroxide, and lithium hydroxide are exemplary. The reaction is preferably conducted in an aprotic solvent such as dimethyl sulfoxide or a solvent such as dioxane, as disclosed in Japanese patent Kokai (Laid Open) No. 60-31517, the complete disclosure of which is incorporated herein by reference, to obtain a highly pure product.

In the present invention, the stilbene type phenolic compound represented by the general formula (3) can be produced by diverse methods available to those skilled in the art. Exemplary methods include among others: (1) rearrangement reaction of a chloro derivative prepared by the reaction of monochloroacetaldehyde and phenol as described in Liebigs Ann. Chem. 730, 31 (1969), (2) the rearrangement reaction of a chloro derivative prepared by the reaction of chloral and phenol according to Ann., 325, 26 (1902), (3) the reduction of a stilbenequinone according to J. Org. Chem., 18, 261 (1953), (4) a process in which quinonemethide is used as a starting material according to J. Org. Chem., 34(11), 3404 (1969), (5) the de-methylation of dimethoxystilbene according to Recl. Trav. Chim. Pays-Bas., 80, 775 (1961), or, for instance, (6) the condensation reaction of a benzaldehyde derivative according to Synthesis, 1989, 883. The complete disclosures of all preparation methods are hereby incorporated by reference.

A trans-stilbene type phenolic compound is represented by the general formula (3). Suitable trans-stilbene-type phenols include the trans-isomers of 4,4'-dihydroxystilbene; 4,4'-dihydroxy-3,3'-dimethylstilbene; 3,3'-diethyl4,4'-dihydroxystilbene; 4,4'-dihydroxy-3,3'-dipropylstilbene; 3,3'-diamyl4,4'-dihydroxystilbene; 3,3'-dihexyl4,4'-dihydroxystilbene; 3,3'-dicyclohexyl-4,4'-dihydroxystilbene; 2,2'-dihydroxy-3,3', 5,5'-tetramethylstilbene; 4,4'-dihydroxy-3,3', 5,5'-tetramethylstilbene; 4,4'-dihydroxy-3,3 '-di-t-butyl stilbene; 4,4'-dihydroxy-3,3'-di-t-butyl-5,5'-dimethylstilbene; 4,4'-dihydroxy-3,3'-di-t-butyl-6,6'-dimethylstilbene; 2,2'-dihydroxy-3,3'-di-t-butyl-6,6'-dimethylstilbene; 2,4'-dihydroxy-3,3'-di-t-butyl-6,6'-dimethylstilbene; and 4,4'-dihydroxy-3,3', 5,5'-tetra-t-butylstilbene.

Particularly preferred phenols include the trans-isomers of 4,4'-dihydroxystilbene; 2,2'-dihydroxy-3,3'-5,5'-tetramethylstilbene; 4,4'-dihydroxy-3,3', 5,5'-tetramethylstilbene; 4,4'-dihydroxy-3,3'-di-t-butyl-5,5'-dimethylstilbene; 4,4'-dihydroxy-3,3'-di-t-butyl-6,6'-dimethylstilbene; 2,2'-dihydroxy-3,3'-di-t-butyl-6,6'-dimethylstilbene; and 2,4'-dihydroxy-3,3'-di-t-butyl-6,6'-dimethylstilbene. These phenols are preferred because of their facile synthesis, desired properties, and economical starting materials.

The photoisomerization reaction of the trans-stilbene type epoxy resin or phenolic compounds can be executed by the irradiation with use of ultraviolet light generated from UV emission equipment known to those skilled in the art. The material subject to irradiation can be in the form of solution, melt, or solid. Solvent can be employed, and the solvent will generally be one or more organic solvent. There are no particular limitations to the solvent provided that neither photopolymerization nor the practice of the invention are impaired. Suitable solvents for the photoisomerization include hydrocarbons, including aromatic and acyclic hydrocarbons. Examples include the aromatic hydrocarbons toluene and xylene. Halogenated hydrocarbons can be used and examples include halobenzenes such a chlorobenzene. Ethers can be used such as, for example, dioxane and tetrahydrofuran. Alcohols can be used, and examples include alkanols such as the lower-alkanols exemplified by methanol, ethanol, propanol, butanol, pentanol, and hexanol. Ketones can be used including, for example, methyl isobutyl ketone, methyl ethyl ketone, acetone, cyclopentanone, and cyclohexanone. Aprotic polar solvents can be used such as, for example, dimethylsulfoxide, dimethylacetamide, dimethyformamide, and N-methylpyrolidone. Glycols can be used such as, for example, ethylene glycol, propylene glycol, diethylene glycol, dipropylene glycol, ethylene glycol monomethyl ether, and propylene glycol monomethyl ether. Acidic solvents can be used such as, for example, lower alkyl carbonic acids including acetic acid, chloroacetic acid, and butyric acid. The above solvents can be used singly or in a combination.

Suitable irradiation equipment for the photoisomerization reaction is known to those skilled in the art and includes a low-pressure mercury lamp, a high-pressure mercury lamp, a Xenon lamp and lasers such as an excimer laser. The efficiency of the isomerization reaction is influenced by the absorbance of the absorption band of the compound and the wave length of emission lines of the light source. It is therefore preferable to select the light source by matching its UV emission to the wavelength range of the absorption band in ultra-violet and visible regions of the trans-isomer. In general, the region of the wavelength of the emission lines to be utilized is about between about 250 and about 400 nm.

Upon UV-irradiation, the broad absorption peak at 307 nm of the trans isomer in UV-spectrum was diminished.

The stilbene type epoxy resin consisting of at least 10% cis-isomer content can be produced by ultraviolet light induced photoisomerization of materials containing the trans-stilbene type phenolic compound represented by general formula (3) to yield the corresponding cis-isomer represented by formula (4). Following photoisomerization, reaction of this phenolic stilbene with epihalohydrin can be executed in the presence of at least one suitable basic substance. Photoisomerization of the epoxy compound can be carried out in the same manner as for the phenolic compound.

The glycidyl etherification reaction of the stilbene type phenol consisting of at least about 10% cis-isomer content can be conducted according to the well-known process of the glycidyl etherification of the phenolic compounds as described above.

In general, the $^1$H-NMR method can be used to identify the cis-stilbene type epoxy resins and determine the cis-isomer content. Spectral peaks for stilbene C=C—H vinylic protons and for aromatic protons in the cis-isomer are shifted to a higher field (lower ppm) than for the corresponding trans-isomer. In particular, peaks for the cis-isomer stilbene C=C—H vinylic proton are observed at the high field region of 6.5 ppm or less. In this region, peaks for the trans-isomer are not observed. Other methods to determine the cis-isomer content include $^{13}$C NMR and infrared spectroscopy. In general, the preferred method is NMR because of convenience. Methods may be used applicable to both soluble and insoluble materials. For an insoluble product, cis-isomer content can be determined by NMR for solids.

Cis-isomer content or isomerization ratio is defined as:

$$\frac{\text{mol cis-isomer}}{\text{mol cis-isomer + mol trans-isomer}} \times 100(\%)$$

The cis-isomer content or isomerization ratio can be controlled by the amount and time of irradiation, concentration of stilbene derivative during photoisomerization, and solvent selection. In general, the cis-isomer content is at least about 10%, and preferably at least about 20%, and more preferably at least about 40% in order to obtain desired properties. In general, an isomerization ratio of less than 10% is too low to obtain the desired properties. To obtain a pure or essentially pure cis-isomer, purification such as recrystallization, fractional crystallization, or chromatography is necessary. Purification procedures can be carried out by ordinary methods.

There are no particular limitations to the concentration of stilbene units within the resin provided that the concentration is effective in achieving the desirable advantages of the present invention. The person of skill in the art can determine the effective amount based on among other factors melting point, viscosity, and processability studies of the resins or resin precursors. The effective amount may vary depending on the application and resin formulation. However, in general, the concentration of stilbene units will be between about 0.1 and about 20 wt. %, and in particular, between about 1 and about 10 wt. %.

In general, epoxy resins of semi-solid and solid form can be used. The epoxy resin melting point will be in general not higher than about 250° C., and preferably, not higher than about 140° C. In general, the epoxy resin viscosity can be between about 0.01 poise and about 1 poise, and preferably, between about 0.01 poise and about 0.2 poise at a temperature of 150° C. The epoxy resins can be processed, in general, at temperatures between about 20° C. and about 250° C., and preferably, between about 150° C. and about 200° C. The molecular weights of the epoxy resins before substantial cure can be between about 300 g/mol and about 800 g/mol, and preferably, between about 350 g/mol and about 500 g/mol. The precise molecular weight of a resin, however, may be difficult to determine after cure for cross-linked resins.

The epoxy resins of the present invention can be processed and cured by methods known to those of skill in the art. The processed epoxy resins can be used in forming various configuration and forms as known to those of skill in the art. The epoxy resins can be blended with other resins as known by those of skill in the art. Various additives, fillers, flexibilizers, extenders, and the like can be added to the resin. If desired, foams and powder coatings can be used.

The epoxy resins can be used in casting, potting, molding, impregnation, and encapsulation technologies. In particular, encapsulation is a preferred application. Polyesters, epoxies, urethanes, and silicones are generally useful in these arts.

Suitable epoxy resin and methods for this preparation are described in Japanese Patent Application No. 7-136760 filed Jun. 2, 1995, the complete disclosure of which is hereby incorporated by reference.

EXAMPLES

The Examples further describe the present invention, but are not intended to restrict its scope.

Example 1

A methyl isobutyl ketone solution containing 5% of the stilbene phenolic compound 4,4'-bis(2,3-epoxypropoxy)-3, 3', 5,5'-tetramethylstilbene (epoxy resin) was irradiated with ultraviolet light by a high-pressure mercury lamp to induce photoisomerization. The stilbene derivative subjected to photoisomerization was prepared by conventional methods. It was prepared from 2,6-xylenol and chloroacetaldehyde by dehydration reaction and rearrangement reaction accompanied with dehydrochlorination as described in Liebigs Ann. Chem., 730, 31, 1960, the complete disclosure of which is hereby incorporated by reference. This was followed by conventional glycidyletherification. After this photoisomerization, the solution was distilled under reduced pressure to yield a yellow material. The $^1$H-NMR spectra of the stilbene derivative before irradiation and the stilbene derivative after irradiation are illustrated in FIG. 1. The NMR spectra were measured with use of a Brucker AC200P spectrometer. After irradiation, the spectra showed appearance of the high field peaks characteristic of the cis-olefin which were not observed before irradiation. In the $^1$H-NMR spectrum, the cis-stilbene type epoxy is characterized by the appearance of the peaks at high field of 7 ppm or less due to the proton attached to the unsaturated carbon-carbon double bond.

The amount of isomerization can be calculated from the intensity of the peaks in the spectrum. For this sample, the calculation indicated that 27% of the trans-isomer was converted to the cis-isomer. Irradiation of a 0.1 % solution of the same sample resulted in 50% isomerization to the cis-isomer.

Table 1 shows the melting points of these resins obtained together with that of the resin before irradiation. The melting points were measured with use of a Yanagimoto MP-S3 melting point measurement apparatus, and the melting point was determined to be the temperature at which the sample completely melted.

TABLE 1

Relationship between cis isomerization ratio and melting point.

| cis isomerization ratio (%) | melting point (°C.) |
|---|---|
| 0 | 151 |
| 27 | 135 |
| 50 | 120 |

Table 2 shows the temperature dependence of the viscosity of the resin having the cis isomerization ratio of 27% and the resin before photoirradiation. The viscosity was measured by Contraves Leomat 115A viscosity measurement apparatus.

TABLE 2

Viscosity temperature dependence before and after photoisomerization

| cis isomerization ratio (%) | viscosity (poise) | | |
|---|---|---|---|
| | 150° C. | 160° C. | 170° C. |
| 0 | — | 0.17 | 0.10 |
| 27 | 0.15 | 0.08 | 0.04 |

The stilbene type epoxy resin of the present invention, consisting of 10% or more of the cis-isomer, exhibits surprisingly different properties from those of a 100% trans-stilbene type epoxy resin, such as lower melting point and a lower viscosity. In the photoisomerization reaction, it becomes possible to control, e.g., tailor, the desired properties by the change of the photo irradiation condition. By such control of properties, the operation efficiency and the molding characteristics are improved, and the resin has superior economic and production efficiencies such as reduced processing times. The number of useful applications of the resins can be extended. The melting point of the epoxy resin greatly varies according to the content of the cis-isomer, so it is possible to control the melting point of the resin in the wide range from a room temperature to 150° C., which allows for flexibility in tailoring the resins for particular purposes and uses. The present epoxy resin is useful for formulating adhesives, paints, and electric and electronic materials, such as insulation materials and laminated plates and the like. The epoxy resin is particularly useful to encapsulate electronic devices and to the process for producing electronic devices.

All references cited herein are hereby incorporated by reference.

While the invention has been described in detail and with reference to specific embodiments thereof, it will be apparent to those of ordinary skill in the art that various changes and modifications can be made therein without departing from the spirit and scope thereof.

What is claimed is:

1. A process comprising the step of photoisomerizing an epoxy resin containing stilbene linkages, wherein said photoisomerization results in a cis-isomer content in the epoxy resin of at least about 10% by mole.

2. A process according to claim 1, wherein said epoxy resin is uncured and contains the structural unit having epoxy functional groups represented by formula (2):

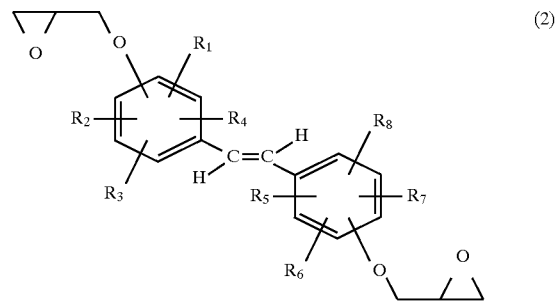

or alternatively if said epoxy resin is partially cured or cured, at least some of said epoxy functional groups represented by formula (2) are reacted by said cure, wherein $R_1$ to $R_8$ independently represent an acyclic or cyclic alkyl group, a hydrogen atom, or a halogen atom.

3. A process according to claim 1, wherein said cis-isomer content is at least 20% by mole.

4. A process according to claim 1, wherein said cis-isomer content is at least 40% by mole.

5. A process comprising the steps of:

photoisomerizing a phenolic stilbene compound to yield an isomerized phenolic stilbene compound, wherein said photoisomerization results in a cis-isomer content of at least about 10% by mole, or in the alternative, about 100% by mole, and converting said isomerized phenolic stilbene compound to an epoxy resin by reaction with epihalohydrin in the presence of a base.

6. A process according to claim 5, wherein said phenolic stilbene compound is represented by formula (3) in its trans-isomeric form as:

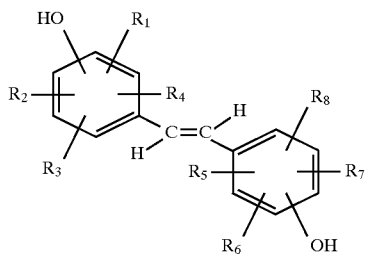

wherein $R_1$ to $R_8$ independently represent an acyclic or cyclic alkyl group, a hydrogen atom or a halogen atom;

and said isomerized phenolic stilbene compound is represented by the general formula (4) in its cis-isomeric form as:

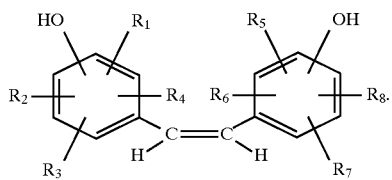

7. A process according to claim 5, wherein said isomerization results in a cis-isomer content of at least about 20% by mole.

8. A process according to claim 5, wherein said isomerization results in a cis-isomer content of at least about 40% by mole.

9. A process for producing a stilbene epoxy resin comprising the step of irradiating with ultraviolet light a trans-stilbene epoxy resin represented by the general formula 2:

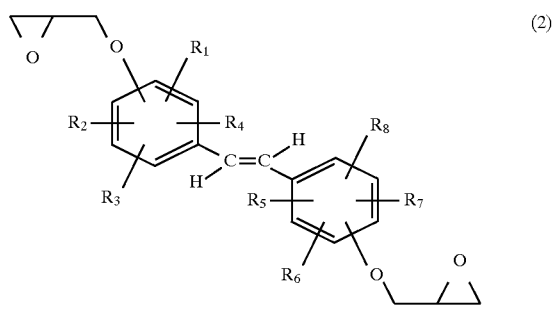

wherein $R_1$ to $R_8$ independently represent an acyclic or cyclic alkyl group, a hydrogen atom or a halogen atom.

10. A process for producing an epoxy resin comprising the steps of:

(i) irradiating with ultraviolet light a trans-stilbene phenol represented by the general formula (3):

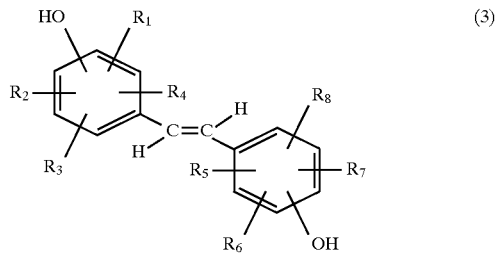

wherein $R_1$ to $R_8$ independently represent an acyclic or cyclic alkyl group, a hydrogen atom or a halogen atom, to yield a stilbene phenol represented by formula (4):

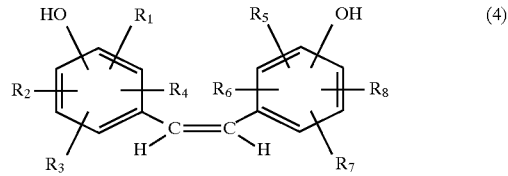

wherein $R_1$ to $R_8$ independently represent an acyclic or cyclic alkyl group, a hydrogen atom or a halogen atom; and (ii) reacting said stilbene phenol represented by formula (4) with epihalohydrin in the presence of a base.

* * * * *